United States Patent [19]

Nishimura et al.

[11] 3,948,928

[45] Apr. 6, 1976

[54] 3-SUBSTITUTED-1,2-BENZISOXAZOLES AND PHARMACEUTICALLY ACCEPTABLE ACID ADDITION SALTS THEREOF

[75] Inventors: Haruki Nishimura, Ikeda; Masanao Shimizu, Kobe; Hitoshi Uno, Takatsuki; Tetsuo Hirooka, Settsu; Yoshinobu Masuda, Osaka; Mikio Kurokawa, Kobe, all of Japan

[73] Assignee: Dainippon Pharmaceutical Co., Ltd., Osaka, Japan

[22] Filed: Mar. 12, 1973

[21] Appl. No.: 340,195

[30] Foreign Application Priority Data
Mar. 17, 1972 Japan.............................. 47-27865
Mar. 17, 1972 Japan.............................. 47-27866

[52] U.S. Cl. ............... 260/307 DA; 260/247.5 EP; 260/268 BC; 260/256.4 H; 424/248; 424/250; 424/251; 424/272
[51] Int. Cl.²....................................... C07D 261/20
[58] Field of Search ............................ 260/307 D

[56] References Cited
UNITED STATES PATENTS
3,673,188   6/1972   Harsanyi et al................ 260/288 R OTHER PUBLICATIONS
Smith, P.A.S. — *Chemistry of Open Chain Organic Nitrogen Compounds* — Vol. II — W. A. Benjamin, Inc. (1966) — p. 93.

*Primary Examiner*—Raymond V. Rush
*Attorney, Agent, or Firm*—Stevens, Davis, Miller & Mosher

[57] ABSTRACT

3-Substituted-1,2-benzisoxazole derivative of the following formula:

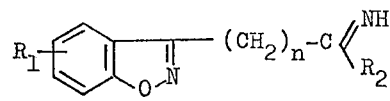

wherein $R_1$ is hydrogen, hydroxy, nitro, alkyl, alkoxy, halogen or amino; $R_2$ is hydroxyamino, amino, hydrazino, mono- or di- alkyl substituted amino, aralkylamino, acyloxyamino, morpholino, piperazine which is unsubstituted or substituted with alkyl, aralkyl or aryl at 4 position, or pyrrolidino, or $R_2$ may combine with imino group and form together with the adjacent carbon atom a heterocyclic ring such as imidazoline or tetrahydropyrimidine; and $n$ is an integer of 0 to 3, and its pharmaceutically acceptable acid addition salt, and preparation thereof. The present compounds show valuable pharmacological properties, such as anti-reserpine activity, central nervous depressing activity, anti-hypertensive activity and l-dopa potentiating activity.

10 Claims, No Drawings

3-SUBSTITUTED-1,2-BENZISOXAZOLES AND PHARMACEUTICALLY ACCEPTABLE ACID ADDITION SALTS THEREOF

The present invention relates to a new and useful benzisoxazole derivative, more particularly relates to a 3-substituted-1,2-benzisoxazole derivative, its pharmaceutically acceptable acid addition salt and preparation thereof.

The 3-substituted-1,2-benzisoxazole derivative of the present invention can be illustrated by the following formula:

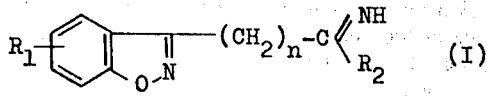

wherein $R_1$ is hydrogen, hydroxy, nitro, alkyl, alkoxy, halogen or amino; $R_2$ is hydroxyamino, amino, hydrazino, mono- or dialkyl substituted amino, aralkylamino, acyloxyamino, morpholino, piperazino which is unsubstituted or substituted with alkyl, aralkyl or aryl at 4 position, or pyrrolidino, or $R_2$ may combine with imino group and form together with the adjacent carbon atom a heterocyclic ring such as imidazoline

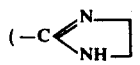

or tetrahydropyrimidine

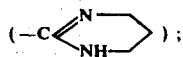

and $n$ is an integer of 0 to 3.

The term "alkyl" used in the present specification means a straight or branched alkyl having 1 to 5 carbon atoms. The term "alkoxy" means a straight or branched alkoxy having 1 to 5 carbon atoms. The term "acyl" means a residue of an acid selected from an aromatic carboxylic acid, aliphatic carboxylic acid and carbonic acid. The term "aryl" means phenyl, halogenophenyl, tolyl, alkoxyphenyl, and the like.

The benzisoxazole ring may be substituted by one or more groups defined for $R_1$, i.e. the benzene ring of the benzisoxazole ring may be substituted by 1 to 3 groups, which may be the same or different.

When $R_2$ is a primary or secondary amino group, the compound of formula (I) may form tautomer, which can be illustrated, for instance, in case of $R_2$ is hydroxyamino, by the following scheme:

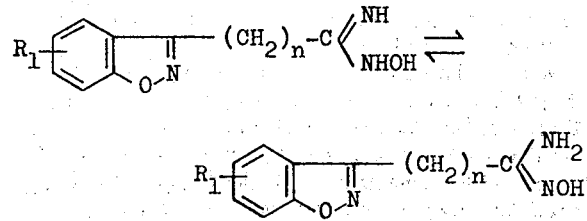

The most suitable group defined for $R_2$ may be hydroxyamino or in case of combining with imino group to form an imidazoline ring.

The preferred examples of the present 3-substituted-1,2-benzisoxazole derivatives may be 1,2-benzisoxazole-3-acetamidoxime, 1,2-benzisoxazole-3-acetamidine, 6-methoxy-1,2-benzisoxazole-3-acetamidoxime, 0-benzoyl-1,2-benzisoxazole-3-acetamidoxime, 0-ethoxycarbonyl-1,2-benzisoxazole-3-acetamidoxime, 0-acetyl-1,2-benzisoxazole-3-acetamidoxime, 3-(2-imidazolin-2-yl)methyl-1,2-benzisoxazole, 6,7-dihydroxy-3-(2-imidazolin-2-yl)methyl-1,2-benzisoxazole, 7-methyl-3-(2-imidazolin-2-yl)-methyl-1,2-benzisoxazole, 1,2-benzisoxazole-3-propionamidoxime, 1,2-benzisoxazole-3-(N-methyl)acetamidine, 5-fluoro-1,2-benzisoxazole-3-acetamidoxime and 5-fluoro-3-(2-imidazolin-2-yl)methyl-1,2-benzisoxazole and hydrochloride thereof.

The present 3-substituted-1,2-benzisoxazole derivatives and their salts can be prepared by reacting a reactive derivative of an acid amide having the following formula:

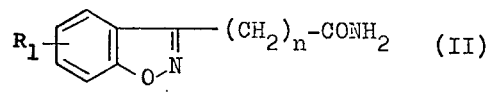

wherein $R_1$ and $n$ are the same as defined above, or its salt with an amine derivative having the following formula:

wherein $R_2'$ is hydroxyamino, amino, hydrazino, mono- or dialkyl substituted amino, aralkylamino, acyloxyamino, morpholino, piperazino which is unsubstituted or substituted with alkyl, aralkyl or aryl at 4 position, pyrrolidino, 2-aminoethylamino or 3-aminopropylamino.

The reactive derivative of an acid amide of the formula (II) means the compounds having the following formulae:

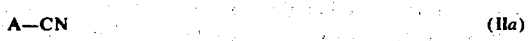

and

wherein A is

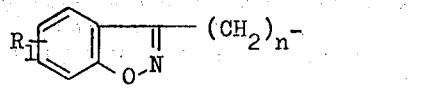

in which $R_1$ and $n$ are the same as defined above.

The most suitable starting material for the preparation of each desired compound (I) may be optionally selected from the reactive derivatives above-mentioned according to the reactivity thereof.

For the reaction of the compound (III) with the reactive derivative of the compound (II), the compound (III) may be used in an equimolar or somewhat excess amount to the reactive derivative the compound (II), and further may be used in a free base or in a form of salt with an appropriate acid. When the compound (III) is used in a form of its salt, the reaction may be preferably carried out in the presence of a base, such as alkali metal alcoholate (e.g. sodium methoxide, potassium methoxide, sodium ethoxide, or potassium ethoxide), sodium carbonate, potassium carbonate, sodium hydrogen carbonate, potassium hydrogen carbonate, or triethylamine.

The more detailed descriptions of the preparation of the desired compounds (I) of the present invention and their salts are disclosed below. For convenience, the descriptions are categorized into sections according to the starting reactive derivatives (IIa) to (IIe).

1. In case of using nitrile compound (IIa)

The nitrile compound of the formula (IIa) is reacted with the compound (III) by a conventional method to give the desired compound (I).

The reaction can be carried out in the presence or absence of an inert solvent, such as absolute or aqueous aliphatic alcohol (e.g. methanol or ethanol), benzene, toluene, 1,2-dichlorobenzene, and dimethylformamide. The reaction temperature is not specifically defined and usually in a range of cooled temperature to elevated temperature.

When ethylenediamine or 1,3-propanediamine is used as the compound (III), the reaction can be preferably carried out in the presence of small amount of carbon disulfide in an inert solvent or without solvent by heating at 100° to 185°C. When ammonia or a primary amine is used as the compound (III), the reaction can be carried out in the presence of aluminum chloride, zinc chloride or ammonium halide (e.g. ammonium chloride or ammonium bromide), or by using the amine compounds in a form of thiocyanate, in an inert solvent or without solvent by heating at 100° to 185°C, if necessary under a pressure.

2. In case of using imino ether compound (IIb)

An imino ether compound of the formula (IIb) or its salt is reacted with the compound (III) by a conventional method to give the desired compound (I) or its salt.

The reaction can be carried out at a temperature from cooled to elevated temperature (e.g. from −5° to 100°C), in the presence of an inert solvent, such as alcohol (e.g. methanol or ethanol) or the like.

3. In case of using iminothio ether compound (IIc)

An iminothio ether compound of the formula (IIc) or its salt is reacted with the compound (III) by a conventional method to give the desired compound (I) or its salt.

The reaction can be carried out at a temperature from cooled to elevated temperature (e.g. from −5° to 100°C), in the presence of an inert solvent, such as alcohol (e.g. methanol or ethanol) or the like.

4. In case of using thioamide compound (IId)

A thioamide compound of the formula (IId) is reacted with the compound (III) by a conventional method to give the desired compound (I).

The reaction can be carried out in the presence or absence of an inert solvent at an elevated temperature (e.g. from 50° to 150°C). The suitable solvent may be an absolute or aqueous alcohol (e.g. methanol or ethanol) but other inert solvent may be also used.

5. In case of using amidine compound (IIe)

An amidine compound of the formula (IIe) or its salt is reacted with the compound (III) by a conventional method to give the desired compound (I) or its salt.

The reaction can be carried out in an absolute or aqueous alcohol (e.g. methanol or ethanol) or other inert solvent at a temperature from cooled to elevated temperature (e.g. from −5° to 100°C).

In the above reactions, when ethylenediamine or 1,3-propanediamine is reacted with the reactive derivative of the compound (II), an intramolecular reaction occurs to form a ring compound with the elimination of ammonia. The reaction can be illustrated by the following reaction scheme:

Reactive derivative of the compound (II) + $H_2N-(CH_2)_{2-3}-NH_2 \rightarrow$ 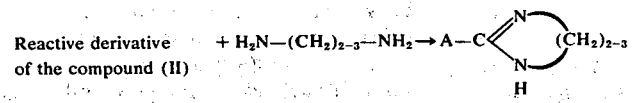

wherein A is the same as defined above.

The starting reactive derivatives of the compound (II) can be prepared by the following methods.

The compound (IIa) can be prepared by heating the compound (II) in the presence of dehydrating agent (e.g. phosphorus oxychloride, thionyl chloride or phosphorus pentachloride). The compound (IIb) can be prepared by dissolving the compound (IIa) in an alcohol and passing through thereto gaseous dry hydrogen chloride to give the hydrochloride of the compound (IIb). The compound (IId) can be prepared by heating the compound (II) in the presence of phosphorus pentasulfide in a solvent (e.g. benzene, toluene or xylene). The salt of compound (IIc) can be prepared by reacting the compound (IId) with an alkyl halide in acetone at elevated temperature. The compound (IIe) is one of the desired compound (I), in which $R_2$ is amino.

The desired compound (I) wherein $R_2$ is hydroxyamino can be alternatively prepared by reacting a hydroximic acid derivative of the following formula:

wherein X is halogen or alkoxy and A is the same as defined above, with ammonia.

The reaction is carried out in an inert solvent at a temperature of from cooled to elevated temperature (e.g. from −5° to 180°C). The suitable solvent may be an alcohol (e.g. methanol or ethanol), chloroform, dioxane, or the like.

When X in the formula (IV) is halogen, i.e. hydroximic acid halide derivative is used, the compound (IV) is also reacted with hydroxylamine in the presence of an alkali at a temperature of from cooled to elevated temperature (e.g. from −5° to 100°C) to give the desired compound (I) wherein $R_2$ is hydroxyamino. Furthermore, the desired compound (I) wherein $R_2$ is hydroxyamino can be also prepared by reacting the hydroximic halide derivative with a base such as triethylamine in an inert solvent such as chloroform to give nitrile oxide compound and reacting the intermediate nitrile oxide compound with ammonia.

These reactions can be illustrated by the following reaction schemes:

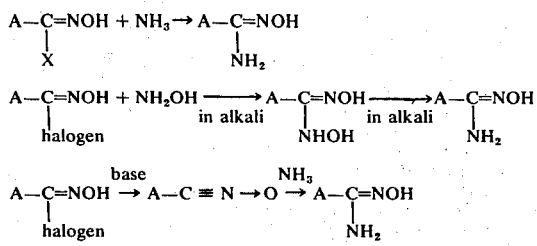

wherein A and X̄ are the same as defined above.

The starting compound (IV) used in the above reaction can be prepared by reacting an aldehyde derivative of the formula: A—CHO wherein A is the same as defined above, with hydroxylamine to give an aldoxime derivative and reacting the resultant aldoxime derivative with gaseous halogen (e.g. chlorine gas) in an inert solvent (e.g. chloroform or ether) to give the hydroximic halide derivative. The hydroximic halide derivative thus obtained is reacted with an alkali metal alcoholate (e.g. sodium methoxide, potassium methoxide, sodium ethoxide or potassium ethoxide) in an alcohol to give the compound (IV) wherein X is alkoxy.

The desired compound (I) wherein $R_2$ is acyloxyamino can be also prepared by acylating the amidoxime compound ($R_2$ is hydroxyamino) with a conventional acylating agent. The reaction can be illustrated by the following reaction scheme:

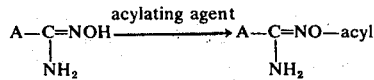

wherein A is the same as defined above.

In the above reaction, when a compound having hydroxy or amino substituent on the benzene ring is used as the starting amidoxime compound, the desired compound may be contaminated with a compound, in which the hydroxy or amino group is also acylated, and therefore, the reaction may be preferably applied to the compound having no such hydroxy or amino substituent on the benzene ring.

The reaction can be carried out in the presence of an appropriate condensing agent in an inert solvent at a temperature of from cooled to elevated temperature (e.g. from −5° to 115°C). The suitable example of the acylating agent may be carboxylic acid halide, carboxylic acid anhydride, ketene, alkyl halogenoformate or the like. The suitable condensing agent may be an alkali metal carbonate (e.g. sodium carbonate, potassium carbonate), pyridine, triethylamine, or the like. The suitable inert solvent may be acetone, methyl ethyl ketone, chloroform, dioxane, tetrahydrofuran, or the like.

The desired 3-substituted-1,2-benzisoxazole derivative (I) of the present invention can be prepared in a form of free base or its salt according to the kind of the starting material and the reaction conditions. When the compound (I) is obtained in a form of its salt, it can be easily converted into its free base by a conventional method, for instance, by treating the salt with an alkaline reagent such as alkali metal hydroxide or carbonate (e.g. sodium hydroxide, potassium hydroxide, sodium carbonate, or potassium carbonate) or ion-exchange resin. On the other hand, when the compound (I) is obtained in a form of free base, it can be easily converted into its pharmaceutically acceptable acid addition salt by a conventional method, for instance, by treating with an inorganic or organic acid (e.g. hydrochloric acid, phosphoric acid, sulfuric acid, hydrobromic acid, hydroiodic acid, citric acid, lactic acid, maleic acid, malic acid, tartaric acid, acetic acid, benzoic acid, or ascorbic acid).

The present 3-substituted-1,2-benzisoxazole derivative (I) and their pharmaceutically acceptable acid addition salts show valuable pharmacological properties in central nervous system and circulation system. For instance, the present compounds show excellent anti-reserpine activity, central nervous depressing activity, anti-hypertensive activity and 1-dopa potentiating activity, and clinically the present compounds are useful as antidepressant, anti-hypertensive, or antiparkinsonian drug.

Some of the test results, by which the utility of the present compounds is confirmed, are described below.

TEST 1

Anti-reserpine activity

The anti-reserpine activity of the test compounds was studied by the antagonism against the hypothermy induced by reserpine on male dd YS-mice, weighing 18 to 20 g, each group being 5 mice. The test compounds were orally administered in a dose of 100 mg/kg and simultaneously reserpine was intraperitoneally administered in a dose of 5 mg/kg to the mice. The body temperature was measured on the rectal temperature of the mice at 4 hours after the administration of the test compounds by thermister BMG III-130, made by Shibaura Electric Co., Ltd.

When reserpine was administered in a dose of 5 mg/kg, the body temperature was lowered about 7° to 10°C at 4 hours after administration. Against the hypothermy induced by reserpine, the compounds of the present invention showed excellent antagonism as shown in Table 1.

Table 1

| Test compounds* | Inhibition (%) | Ratio to AMT |
|---|---|---|
| 1 | 66.9 | 1.37 |
| 2 | 64.9 | 1.33 |
| 3 | 57.1 | 1.17 |
| 4 | 51.9 | 1.06 |
| 5 | 69.2 | 1.42 |
| 6 | 58.1 | 1.12 |
| Amitriptyline | 48.9 | 1.00 |

[REMARK] *The test compounds are as follows:
1: 3-(2-Imidazolin-2-yl)methyl-1,2-benzisoxazole hydrochloride
2: 1,2-Benzisoxazole-3-acetamidoxime hydrochloride
3: O-Benzoyl-1,2-benzisoxazole-3-acetamidoxime
4: 7-Methyl-3-(2-imidazolin-2-yl)methyl-1,2-benzisoxazole hydrochloride
5: 6-Methoxy-1,2-benzisoxazole-3-acetamidoxime hydrochloride
6: 1,2-Benzisoxazole-3-propionamidoxime hydrochloride
Amitriptyline (AMT): 3-(10,11-Dihydro-5H-dibenzo[a,d]-cyclohepten-5-ylidene)-N,N-dimethylpropylamine which has been widely used as an antidepressant.

TEST 2

1-Dopa potentiating activity

To dd YS-mice, weighing 18 to 20 g (each group being 10 mice) was intraperitoneally administered 300 mg/kg of 1-dopa: 3-(3,4-dihydroxyphenyl)-L-alanine. The mice were entered into a plastic cage having 15 × 15 cm$^2$ in size and allowed to live gregariously and then the symptom of the mice was observed. The test compounds were orally administered to the mice at one hour before the administration of 1-dopa. The activity of the test compounds was calculated by the mortality. The results are shown in Table 2. As made clear from the test results, the present compound showed excellent 1-dopa potentiating activity even in less dose than that of amantadine: 1-aminoadamantane which has been known to have 1-dopa potentiating activity.

Table 2

| Test compounds | Dose (mg/kg) | Number of dead mice/ number of used mice |
|---|---|---|
| 1* | 20 | 1/10 |
|  | 50 | 3/10 |
|  | 100 | 7/10 |
| Amantadine | 100 | 0/10 |
|  | 200 | 3/10 |
|  | 300 | 5/10 |
| Control | 0 | 0/10 |

[REMARK] *1,2-Benzisoxazole-3-acetamidoxime hydrochloride

TEST 3

Anti-hypertensive activity

A. Renal hypertensive rats

Male Wistar rats weighing 180 to 200 g and having a blood pressure of 125 to 145 mmHg were anesthetized with ether and the left abdominal wall of rats was cut and thereby the renal artery was laid bare. The origin part of the aorta was stripped off and to the renal artery was fixed a silver clip which was made by two-folding at interval of 0.2 mm a silver thin board having 2.0 mm in width, 6.0 mm in length and 0.3 mm in thickness, and then the abdominal wall was stitched. At 2 months after the operation, the blood pressure of the rats was increased to 150 or more mmHg. The rats thus treated were used in the test as the renal hypertensive rats.

B. Measurement of blood pressure in rats.

The blood pressure was measured by plethysmographic method, in which the blood pressure was measured indirectly by using a tail of animal without anesthesia. That is, after being warmed at 38°C for 10 minutes, a tail of rat was pressed by cuff and then the pressure was relieved and thereby the blood flow started again to increase the volume of tail. The blood pressure at that time was measured.

The blood pressure was measured before the administration of test compounds and at 0.5, 1, 3, 5, 7, 9 and 24 hours after the administration of the test compounds. The results are shown in Table 3.

Table 3

| Test compounds* | Dose (mg/kg) p.o. | Decrease percent | Blood pressure Peak time (hr.) | Duration (hr.) |
|---|---|---|---|---|
| 1 | 30 | 38.8 | 3 | 48 |
|  | 10 | 36.3 | 7 | 30 |
|  | 3 | 18.2 | 7 | 24 |
| 2 | 100 | 34.4 | 1–3 | 30 |

Table 3-continued

| Test compounds* | Dose (mg/kg) p.o. | Decrease percent | Blood pressure Peak time (hr.) | Duration (hr.) |
|---|---|---|---|---|
| 3 | 100 | 19.0 | 7 | 24 |
| 4 | 100 | 10.7 | 3 | 30 |
| 5 | 100 | 19.3 | 3 | 24 |
| 6 | 100 | 56.5 | 5 | 30 |
| 7 | 100 | 21.0 | 5 | 72 |

[REMARK] *The test compounds are as follows:
1: 3-(2-Imidazolin-2-yl)methyl-1,2-benzisoxazole hydrochloride
2: 1,2-Benzisoxazole-3-acetamidine hydrochloride
3: 1,2-Benzisoxazole-3-acetamidrazone hydrochloride
4: 1-Phenyl-4-(1,2-benzisoxazole-3-acetimidoyl)-piperazine hydrochloride
5: 1,2-Benzisoxazole-3-(N-methyl)acetamidine hydrochloride
6: 5-Hydroxy-3-(2-imidazolin-2-yl)methyl-1,2-benzisoxazole hydrochloride
7: 6-Hydroxy-3-(2-imidazolin-2-yl)methyl-1,2-benzisoxazole hydrochloride

TEST 4

Anti-hypertensive activity

Spontaneously hypertensive rats were prepared by using male Wistar rats weighing 300 to 350 g and being 20 or more weeks of age. To the spontaneously hypertensive rats were orally administered a suspension of the test compound (10 mg/kg) in 0.5 % aqueous tragacanth solution. The blood pressure in rats was measured at 0.5, 1, 3, 5, 7, 24 and 30 hours after the administration of the test compounds in the same manner as described in Test 3, (B). The results are shown in Table 4.

Table 4

| Test compound* | Dose (mg/kg) p.o. | Decrease percent | Blood pressure Peak time (hr.) | Duration (hr.) |
|---|---|---|---|---|
| 1 | 10 | 16 | 5.0 | 24 |
| 2 | 10 | 14 | 7.0 | 9 |
| 3 | 10 | 22 | 7.0 | 24 |
|  | 1 | 20 | 7–8 | 24 |
| 4 | 10 | 28 | 7.0 | 30 |

[REMARK] *The test compounds are as follows:
1: 5-Hydroxy-3-(2-imidazolin-2-yl)methyl-1,2-benzisoxazole hydrochloride
2: 6-Hydroxy-3-(2-imidazolin-2-yl)methyl-1,2-benzisoxazole hydrochloride
3: 5-Fluoro-1,2-benzisoxazole-3-acetamidoxime hydrochloride
4: 5-Fluoro-3-(2-imidazolin-2-yl)methyl-1,2-benzisoxazole hydrochloride The 3-substituted-1,2-benzisoxazole derivatives (I) and their pharmaceutically acceptable acid addition salts can be administered preferably orally but also parenterally with conventional pharmaceutical carriers in human beings and animals. A clinical dosage of the present compounds depends on disease syndrome, body weight, age and administration method, but it is, in general, in the range of 10 to 500 mg per day, preferably in the range of 50 to 300 mg per day in adult. Further, they can be used in a unit dosage form such as tablets or capsules for oral administration, optionally in combination with suitable adjuvants, such as binders (e.g. methyl cellulose, starch paste, gum acacia, polyvinylpyrrolidone, carboxymethyl cellulose, or hydroxypropyl cellulose), vehicles (e.g. starch, calcium hydrogen phosphate, calcium carbonate, lactose, or cellulose) and lubricants (e.g. magnesium stearate, hardened castor oil, or talc).

The compounds of the present invention can be also prepared for use by dissolving them in a form of its salt under sterile conditions in water or in a physiologically compatible aqueous medium such as saline, and can be stored in ampoules for injection.

The preparations of the present 3-substituted-1,2-benzisoxazole derivatives (I) and their pharmaceutically acceptable acid addition salts are illustrated by the following examples but not limited thereto.

EXAMPLE 1

1,2-Benzisoxazole-3-acetamidoxime and its hydrochloride

In ethanol (15 ml) was dissolved 1,2-benzisoxazole-3-acetonitrile (3.0 g) and thereto was added a solution of hydroxylamine hydrochloride (1.58 g) and sodium carbonate (1.2 g) in water (7.5 ml) under stirring. After heating at 70°C for 3 hours, water (7.5 ml) was added thereto, and the mixture was allowed to stand under cooling. The precipitated crystallines were separated by filtration, washed with water, dried and recrystallized from ethanol to give the desired compound (3.3 g). m.p. 160° to 162°C.

Elementary Analysis: for $C_9H_9N_3O_2$. Calcd: (%) C, 56.54; H, 4.75; N, 21.98. Found: (%) C, 56.62; H, 4.95; N, 22.12.

The product obtained above (3.3 g) was treated with alcoholic hydrochloric acid to give its hydrochloride, which was recrystallized from ethanol-ether to give the pure product (3.7 g). m.p. 161° to 168°C (decomp).

Elementary Analysis: for $C_9H_9N_3O_2.HCl$. Calcd: (%) C, 47.49; H, 4.42; N, 18.46; Cl, 15.57. Found: (%) C, 47.84; H, 4.65; N, 18.22; Cl, 15.70.

EXAMPLE 2

6-Methoxy-1,2-benzisoxazole-3-acetamidoxime hydrochloride

In ethanol (30 ml) was dissolved 6-methoxy-1,2-benzisoxazole-3-acetonitrile (1 g) and thereto was added a solution of hydroxylamine hydrochloride (0.7 g) and sodium carbonate (0.8 g) in water (5 ml) under stirring. After stirring for 4 hours, the mixture was allowed to stand at room temperature overnight. The precipitated crystallines were separated by filtration and added to ethanol containing 20 % of hydrochloric acid. The mixture was stirred for 2 hours and thereto was added ether. The precipitated crystallines were separated by filtration and recrystallized from ethanol-ether to give the desired compound (0.8 g). m.p. 185° to 187°C.

Elementary Analysis: for $C_{10}H_{11}N_3O_3.HCl$. Calcd: (%) C, 46.61; H, 4.69; N, 16.31; Cl, 13.76. Found: (%) C, 46.45; H, 4.44; N, 16.22; Cl, 13.66.

EXAMPLE 3

5-Methoxy-1,2-benzisoxazole-3-acetamidoxime

In ethanol (20 ml) was dissolved 5-methoxy-1,2-benzisoxazole-3-acetonitrile (2.0 g) and thereto was added a solution of hydroxylamine hydrochloride (0.88 g) and sodium carbonate (1.34 g) in water (10 ml). After heating the mixture on water bath at 70° to 80°C for 3 hours, ethanol was distilled off under a reduced pressure. To the residue was added water and the precipitated crystallines were separated by filtration, washed with water and dried to give the desired compound (1.8 g), which was recrystallized from ethanol. m.p. 180° to 183°C.

Elementary Analysis: for $C_{10}H_{11}N_3O_3$. Calcd: (%) C, 54.29; H, 5.01; N, 19.00. Found: (%) C, 54.39; H, 4.87; N, 19.10.

EXAMPLE 4

3-(2-Imidazolin-2-yl)methyl-1,2-benzisoxazole hydrochloride

A mixture of 1,2-benzisoxazole-3-acetonitrile (1.6 g), ethylenediamine (0.7 g) and carbon disulfide (0.2 ml) was heated at 130° to 150°C for 0.5 hour and then allowed to stand at room temperature overnight. to the reaction mixture was added chloroform and the insoluble substance was filtered off. The filtrate was subjected to silica gel column chromatography and eluted with 10 to 20 % methanol-chloroform. The eluates were collected and treated with ethanolic hydrochloric acid to give the hydrochloride. The product was treated with charcoal and then recrystallized from ethanol to give the desired compound (0.4 g). m.p. 223° to 228°C.

EXAMPLE 5

1,2-Benzisoxazole-3-acetamidine hydrochloride

A mixture of 1,2-benzisoxazole-3-acetonitrile (0.34 g) and aluminum chloride (0.54 g) was melted at 90° to 100°C, while dry ammonia gas was passed through thereto for 10 minutes. The reaction mixture was dissolved in aqueous ethanolic hydrochloric acid under cooling and then the solvent was distilled off. The residue was dissolved in a small amount of ethanol-chloroform and subjected to silica gel column chromatography and eluted with 10 % methanol-chloroform. The eluates were collected and recrystallized from ethanol to give the desired compound (0.08 g). m.p. 209° to 212°C.

Elementary Analysis: for $C_9H_9N_3O.HCl$. Calcd: (%) C, 51.07; H, 4.76; N, 19.85; Cl, 16.75. Found: (%) C, 50.99; H, 4.79; N, 19.84; Cl, 17.04.

EXAMPLES 6 TO 23

In the same manner as described in Example 1 or 4, the following compounds were prepared.

7-Methyl-1,2-benzisoxazole-3-acetamidoxime, m.p. 151° to 153°C 6,7-Dimethoxy-1,2-benzisoxazole-3-acetamidoxime hydrochloride, m.p. 195° to 200°C (decomp)

5-Chloro-1,2-benzisoxazole-3-acetamidoxime hydrochloride, m.p. 181.5° to 182.5°C 5-Hydroxy-1,2-benzisoxazole-3-acetamidoxime hydrochloride, m.p. 195° to 199°C (decomp)

6,7-Dihydroxy-1,2-benzisoxazole-3-acetamidoxime, m.p. 226° to 228°C (decomp)

1,2-Benzisoxazole-3-formamidoxime hydrochloride, m.p. 158° to 165°C

7-Methyl-1,2-benzisoxazole-3-acetamidoxime hydrochloride, m.p. 190° to 201°C (decomp)

6-Hydroxy-1,2-benzisoxazole-3-acetamidoxime hydrochloride, m.p. 213° to 218°C.

5-Nitro-1,2-benzisoxazole-3-acetamidoxime, m.p. 183° to 185°C

5-Fluoro-1,2-benzisoxazole-3-acetamidoxime, hydrochloride, m.p. 182° to 190°C (decomp)

4-Methoxy-1,2-benzisoxazole-3-acetamidoxime hydrochloride, m.p. 199° to 201°C 1,2-Benzisoxazole-3-propionamidoxime hydrochloride, m.p. 178° to 186°C 1,2-Benzisoxazole-3-propionamidoxime, m.p. 135° to 138°C 6-Amino-1,2-benzisoxazole-3-formamidoxime, m.p. 250°C (decomp)

6-Chloro-1,2-benzisoxazole-3-formamidoxime hydrochloride, m.p. 191° to 192°C

6-Nitro-1,2-benzisoxazole-3-formamidoxime, m.p. 218° to 221°C

6-Nitro-1,2-benzisoxazole-3-formamidoxime hydrochloride, m.p. 213° to 215°C 3-(2-Imidazolin-2-yl)methyl-7-methyl-1,2-benzisoxazole hydrochloride, m.p. 235° to 240°C (decomp)

EXAMPLE 24

1,2-Benzisoxazole-3-acetamidoxime

In absolute ethanol (5 ml) was dissolved metal sodium (0.16 g) and thereto was further added hydroxylamine hydrochloride (0.46 g). To the solution was added a solution of ethyl 1,2-benzisoxazole-3-acetimidate hydrochloride (0.5 g) in ethanol (2 ml) under ice-cooling and the mixture was stirred for 1 hour. The resulting precipitate was filtered off and the filtrate was condensed and thereto ether was added. The precipitated crystallines were separated by filtration, washed with ether, dried and recrystallized from ethanol to give the desired compound (0.3 g). m.p. 160° to 162°C.

EXAMPLE 25

3-(2-Imidazolin-2-yl)methyl-1,2-benzisoxazole hydrochloride

In ethanol (10 ml) was dissolved ethyl 1,2-benzisoxazole-3-acetimidate hydrochloride (2.0 g) and thereto was added ethylenediamine (0.6 g) under ice-cooling and the mixture was allowed to stand at 5°C overnight. To the mixture was added ethanolic hydrochloric acid and the precipitated crystallines were separated by filtration and recrystallized from ethanol to give the desired compound (1.85 g). m.p. 223° to 228°C.

Elementary Analysis: for $C_{11}H_{11}N_3O \cdot HCl$. Calcd: (%) C, 55.60; H, 5.09; N, 17.68; Cl, 14.92. Found: (%) C, 55.51; H, 5.26; N, 17.53; Cl, 14.96.

EXAMPLE 26

3-(2-Imidazolin-2-yl)methyl-5-methoxy-1,2-benzisoxazole hydrochloride

In ethanol (20 ml) was dissolved ethyl 5-methoxy-1,2-benzisoxazole-3-acetimidate hydrochloride (2.1 g) and thereto was added ethylenediamine (0.59 g) at room temperature. The mixture was stirred at room temperature for 3 hours and then kept in refrigerator overnight. To the mixture was added ethanol (10 ml) containing 20 % hydrochloric acid, and the precipitated crystallines were separated by filtration, washed with ether, dried and recrystallized from ethanol to give the desired compound (2.5 g). m.p. 240° to 252°C (decomp).

Elementary Analysis: for $C_{12}H_{13}N_3O_2 \cdot HCl$. Calcd: (%) C, 53.83; H, 5.27; N, 15.70; Cl, 13.25. Found: (%) C, 53.68; H, 5.19; N, 15.46; Cl, 13.47.

EXAMPLE 27

3-Amidino-6-nitro-1,2-benzisoxazole

In ethanol (100 ml) was dissolved ethyl 6-nitro-1,2-benzisoxazole-3-formimidate hydrochloride (2.0 g) and the mixture was saturated with ammonia by passing through thereto ammonia gas under stirring at room temperature. The mixture was allowed to stand at room temperature overnight and then ethanol was distilled off under a reduced pressure. The crystalline residue was washed with ether and dissolved in water. The solution was neutralized with sodium bicarbonate and extracted with ether. The extract was distilled to remove ether to give the desired compound (1.2 g), which was recrystallized from chloroform. m.p. 182° to 185°C.

Elementary Analysis: for $C_8H_6N_4O_3$. Calcd: (%) C, 46.60; H, 2.93; N, 27.18. Found: (%) C, 46.75; H, 3.00; N, 27.29.

EXAMPLES 28 TO 54

In the same manner as described in Example 24 to 27, the following compounds were prepared.

1,2-Benzisoxazole-6,7-dimethoxy-3-(N-n-butyl)acetamidine hydrochloride, m.p. 77° to 80°C 1,2-Benzisoxazole-6,7-dimethoxy-3-(N-benzyl)acetamidine hydrochloride, m.p. 167° to 170°C 1,2-Benzisoxazole-3-(N-methyl)acetamidine hydrochloride, m.p. 194° to 197°C 1,2-Benzisoxazole-3-acetamidrazone hydrochloride, m.p. 205° to 210°C 1,2-Benzisoxazole-3-acetamidine hydrochloride, m.p. 209° to 212°C 7-Methyl-3-(2-imidazolin-2-yl)methyl-1,2-benzisoxazole hydrochloride, m.p. 235° to 240°C (decomp)

6,7-Dihydroxy-3-(2-imidazolin-2-yl)methyl-1,2-benzisoxazole hydrochloride, m.p. 244° to 248°C (decomp)

3-(1,4,5,6-Tetrahydropyrimidin-2-yl)methyl-1,2-benzisoxazole hydrochloride, m.p. 232° to 244°C (decomp)

3-(2-Imidazolin-2-yl)methyl-1,2-benzisoxazole hydrochloride, m.p. 223° to 228°C (decomp)

5-Hydroxy-3-(2-imidazolin-2-yl)methyl-1,2-benzisoxazole hydrochloride, m.p. 254° to 260°C (decomp)

6-Hydroxy-3-(2-imidazolin-2-yl)methyl-1,2-benzisoxazole hydrochloride, m.p. 255°C (decomp)

6,7-Dimethoxy-3-(2-imidazolin-2-yl)methyl-1,2-benzisoxazole hydrochloride, m.p. 211° to 216°C 5-Chloro-3-(2-imidazolin-2-yl)methyl-1,2-benzisoxazole hydrochloride, m.p. 255° to 260°C 5-Fluoro-3-(2-imidazolin-2-yl)methyl-1,2-benzisoxazole hydrochloride, m.p. 270° to 290°C (decomp)

4-Methoxy-3-(2-imidazolin-2-yl)methyl-1,2-benzisoxazole hydrochloride, m.p. 248° to 258°C (decom)

6-Methoxy-3-(2-imidazolin-2-yl)methyl-1,2-benzisoxazole hydrochloride, m.p. 225° to 230°C (decomp)

3-]2-(2-imidazolin-2-yl)ethyl]-1,2-benzisoxazole hydrochloride, m.p. 210° to 213°C 3-(2-imidazolin-2-yl)-1,2-benzisoxazole hydrochloride, m.p. 248° to 250°C (decomp)

6-Chloro-3-(2-imidazolin-2-yl)-1,2-benzisoxazole hydrochloride, m.p. 250° to 260°C (decomp)

6-Nitro-3-(2-imidazolin-2-yl)-1,2-benzisoxazole hydrochloride, m.p. 255° to 260°C (decomp)

1-Phenyl-4-(1,2-benzisoxazole-3-acetimidoyl)piperazine hydrochloride, m.p. 245° to 250°C (decomp)

1-m-Chlorophenyl-4-(1,2-benzisoxazole-3-acetimidoyl)-piperazine hydrochloride, m.p. 214° to 217°C (decomp)

4-(1,2-Benzisoxazole-3-acetimidoyl)morpholine hydrochloride, m.p. 230° to 235°C (decomp)
1-(1,2-Benzisoxazole-3-acetimidoyl)piperidine hydrochloride, m.p. 233° to 235°C (decomp)
1-Methyl-4-(1,2-benzisoxazole-3-acetimidoyl)piperazine hydrochloride, m.p. 151° to 153°C
1-Benzyl-4-(1,2-benzisoxazole-3-acetimidoyl)piperazine hydrochloride, m.p. 204° to 206°C (decomp)
1,2-Benzisoxazole-3-(N,N-dimethyl)acetamidine hydrochloride, m.p. 220° to 233°C (decomp)

EXAMPLE 55

1,2-Benzisoxazole-3-acetamidoxime

To a solution of hydroxylamine hydrochloride (0.17 g) and sodium carbonate (0.13 g) in water (5 ml) was added a solution of 1,2-benzisoxazole-3-acetamidine hydrochloride (0.21 g) in ethanol (10 ml) and the mixture was heated on water bath at 80°C for 1 hour. The solvent was distilled off under a reduced pressure and to the residue was added water. The mixture was made alkaline with sodium bicarbonate and the precipitated crystalline were separated by filtration, washed with water, dried and recrystallized from ethanol to give the desired compound (0.16 g). m.p. 160° to 162°C.

EXAMPLE 56

1,2-Benzisoxazole-3-acetamidoxime

To a solution of hydroxylamine hydrochloride (0.15 g) and sodium carbonate (0.12 g) in water (2 ml) was added a solution of 1,2-benzisoxazole-3-thioacetamide (0.38 g) in ethanol (4 ml) and the mixture was heated on water bath at 65°C for 4 hours. To the reaction mixture was added water and the precipitated crystallines were separated by filtration, washed with water, dried and recrystallized from ethanol to give the desired compound (0.33 g). m.p. 160° to 162°C.

EXAMPLE 57

3-(2-Imidazolin-2-yl)methyl-1,2-benzisoxazole hydrochloride

A solution of 1,2-benzisoxazole-3-thioacetamide (0.38 g) and ethylenediamine (1.2 g) in ethanol (30 ml) was refluxed on water bath for 20 hours. The solvent was distilled off and the residue was dissolved in chloroform and subjected to silica gel column chromatography and eluted with 10 to 20 % methanol-chloroform. The eluates were collected and treated with ethanolic hydrochloric acid to give the hydrochloride, which was recrystallized from ethanol to give the desired compound (0.13 g). m.p. 223° to 227°C.

EXAMPLE 58

1,2-Benzisoxazole-3-acetamidoxime

In absolute ethanol (10 ml) was dissolved metal sodium (0.05 g) and thereto was further added hydroxylamine hydrochloride (0.14 g). To the solution was added methyl 1,2-benzisoxazole-3-thioacetimidate hydroiodide (0.34 g) and the mixture was stirred at room temperature for one hour and then was heated at 60°C for 10 minutes. The solvent was distilled off under a reduced pressure and to the residue was added water. The aqueous solution was made alkaline with sodium bicarbonate and extracted with chloroform. The chloroform layer was washed with water, dried over anhydrous sodium sulfate and then distilled to remove the solvent. The residue was recrystallized from ethanol to give the desired compound (0.1 g). m.p. 160° to 162°C.

EXAMPLE 59

1,2-Benzisoxazole-3-(N-methyl) acetamidine hydrochloride

To a solution of methylamine (0.35 g) in absolute ethanol (30 ml) was added a solution of methyl 1,2-benzisoxazole-3-thioacetimidate hydroiodide (3.34 g) in absolute ethanol (70 ml) and the mixture was stirred at room temperature for 1 hour and then heated at 50° to 60°C for 10 minutes. The solvent was distilled off under a reduced pressure and to the residue was added water. The solution was made alkaline with sodium bicarbonate and extracted with chloroform. The chloroform layer was washed with water, dried over anhydrous sodium sulfate and then the solvent was distilled off. The residue was treated with ethanolic hydrochloric acid to give the hydrochloride, which was recrystallized from ethanol to give the desired compound (1.1 g). m.p. 194° to 197°C (decomp).

Elementary Analysis: for $C_{10}H_{11}N_3O \cdot HCl$. Calcd: (%) C, 53.22; H, 5.36; N, 18.62; Cl, 15.71. Found: (%) C, 53.33; H, 5.18; N, 18.67; Cl, 15.99.

EXAMPLE 60

1,2-Benzisoxazole-3-acetamidoxime

In a mixture of chloroform (250 ml) and ethanol (250 ml) was dissolved 1,2-benzisoxazole-3-acetohydroximic chloride (0.5 g) and the mixture was saturated with ammonia by passing through thereto ammonia gas under ice-cooling. The mixture was allowed to stand for 0.5 hour and then the solvent was distilled off under a reduced pressure. To the residue was added chloroform and the insoluble substance was filtered off. The filtrate was distilled to remove the solvent and the residue was recrystallized from ethanol to give the desired compound (0.38 g). m.p. 161° to 163°C.

EXAMPLE 61

1,2-Benzisoxazole-3-acetamidoxime

In ethanol (35 ml) was dissolved 1,2-benzisoxazole-3-acetohydroximic acid ethyl ester (0.5 g) and the mixture was saturated with ammonia gas and then heated in a sealed tube at 150°C for 7 hours. The reaction mixture was distilled under a reduced pressure and the oily residue was subjected to silica gel column chromatography and eluted with 5 % methanol-chloroform. The eluates were collected and resulting crystallines were recrystallized from ethanol to give the desired compound (0.05 g). m.p. 160° to 162°C.

EXAMPLE 62

1,2-Benzisoxazole-3-acetamidoxime

In ethanol (10 ml) was dissolved metal sodium (0.4 g) and thereto was further added hydroxylamine hydrochloride (0.8 g). To the solution was added a solution of 1,2-benzisoxazole-3-acetohydroximic chloride (5.0 g) in ethanol (40 ml) under ice-cooling and the mixture was stirred for hour. The mixture was distilled under a reduced pressure to remove the solvent. To the residue was added chloroform and the insoluble substance was filtered off, and the filtrate was subjected to silica gel column chromatography and eluted with 5 % methanol-chloroform. The resulting precipitated crystallines were separated by filtration and recrystallized from ethanol to give the desired compound (1.0 g). m.p. 161° to 163°C.

EXAMPLE 63

1,2-Benzisoxazole-3-acetamidoxime

To a solution of 1,2-benzisoxazole-3-acetohydroximic chloride (0.4 g) in chloroform (80 ml) was added a solution of triethylamine (3.2 g) in chloroform (40 ml) under ice-cooling and the mixture was stirred for 4 hours under ice-cooling. The mixture was distilled under a reduced pressure to remove the solvent. To the residue was added benzene and the precipitate of triethylamine hydrochloride was filtered off. To the filtrate was passed through ammonia gas under ice-cooling for a period of 1 hour and further at reflux temperature for 3 hours. The mixture was distilled under a reduced pressure to remove the solvent and the residue was subjected to silica gel column chromatography and eluted with 5 % methanol-chloroform. The resulting crystallines were recrystallized from ethanol to give the desired compound (0.1 g). m.p. 160° to 162°C.

EXAMPLE 64

0-Benzoyl-1,2-benzisoxazole-3-acetamidoxime

In acetone (130 ml) was dissolved 1,2-benzisoxazole-3-acetamidoxime (2.8 g) and thereto was further added sodium carbonate (1.6 g). To the mixture was added benzoyl chloride (2.1 g) and the mixture was refluxed at 80°C for 0.5 hour. The precipitate was filtered off, and the filtrate was concentrated under a reduced pressure. The resulting crystallines were recrystallized from acetone to give the desired compound (2.7 g). m.p. 169° to 171°C Elementary Analysis: for $C_{16}H_{13}N_3O_3$. Calcd: (%) C, 65.08; H, 4.44; N, 14.23. Found: (%) C, 65.24; H, 4.24; N, 14.13.

EXAMPLE 65

0-(3,4,5-Trimethoxybenzoyl)-1,2-benzisoxazole-3-acetamidoxime

In the same manner as described in Example 64, 1,2-benzisoxazole-3-acetamidoxime (1.4 g) was reacted with 3,4,5-trimethoxybenzoyl chloride (1.7 g) to give the desired compound (1.6 g). m.p. 127° to 129°C.

Elementary Analysis: for $C_{19}H_{19}N_3O_6$. Calcd: (%) C, 59.21; H, 4.97; N, 10.90. Found: (%) C, 59.15; H, 4.99; N, 10.70.

EXAMPLE 66

0-Acetyl-1,2-benzisoxazole-3-acetamidoxime

In acetone (100 ml) was dissolved 1,2-benzisoxazole-3-acetamidoxime (1.9 g) and thereto was added sodium carbonate (1.06 g). To the mixture was added acetyl chloride (1.58 g) under ice-cooling and the mixture was stirred for 0.5 hour, and then treated in the same manner as described in Example 64 and the resulting crystallines were recrystallized from acetone to give the desired compound (1.0 g). m.p. 173° to 176°C (decomp).

Elementary Analysis: for $C_{11}H_{11}N_3O_3$. Calcd: (%) C, 56.65; H, 4.75; N, 18.02. Found: (%) C, 56.59; H, 4.63; N, 18.20.

EXAMPLE 67

0-Ethoxycarbonyl-1,2-benzisoxazole-3-acetamidoxime

In acetone (100 ml) was dissolved 1,2-benzisoxazole-3-acetamidoxime (1.9 g) and thereto was added sodium carbonate (1.6 g). To the mixture was added ethyl chloroformate (3.2 g) under ice-cooling and the mixture was stirred for 0.5 hour. The resulting precipitate was filtered off and the filtrate was distilled under a reduced pressure to remove the solvent. To the residue as added ether and the insoluble substance was filtered off, and the filtrate was distilled to remove the solvent. The residue was recrystallized from ether to give the desired compound (1.0 g). m.p. 113° to 114°C Elementary Analysis: for $C_{12}H_{13}N_3O_4$. Calcd: (%) C, 54.75; H, 4.98; N, 15.96. Found: (%) C, 54.87; H, 4.68; N, 16.07.

EXAMPLE 68

Tablets having the following formulation were prepared.

| | |
|---|---|
| 1,2-Benzisoxazole-3-acetamidoxime hydrochloride | 10 g |
| Lactose | 30 g |
| Crystalline cellulose | 25 g |
| Corn starch | 25 g |
| Hydroxypropyl cellulose | 2 g |
| Talc | 7 g |
| Hardened castor oil | 1 g |

The above materials were mixed together, granulated and made into tablets in accordance with conventional method to give 1000 tablets, each of which weighs 100 mg.

The starting materials used in the above examples were prepared as follows:

A. 6,7-Dihydroxy-1,2-benzisoxazole-3-acetamide:

In methanol (500 ml) was dissolved ethyl 6,7-dihydroxy-1,2-benzisoxazole-3-acetate (19 g) and the mixture was saturated with ammonia by passing through ammonia gas under ice-cooling. The mixture was allowed to stand at room temperature overnight. The reaction mixture was concentrated under a reduced pressure, and to the residue was added ether and the precipitated crystallines were separated by filtration to give the desired compound (12.0 g). m.p. 221° to 223°C.

B. 6-Chloro-1,2-benzisoxazole-3-carboxamide:

In methanol (250 ml) was dissolved 3-methoxycarbonyl-6-chloro-1,2-benzisoxazole (9.5 g) and the mixture was saturated with ammonia by passing through ammonia gas under ice-cooling. The mixture was allowed to stand at room temperature overnight. The reaction mixture was concentrated under a reduced pressure, and the precipitated crystallines were separated by filtration and dried to give the desired compound (8.8 g), which was recrystallized from methanol. m.p. 204° to 207°C.

C. 1,2-Benzisoxazole-3-acetonitrile:

To phosphorus oxychloride (250 ml) was added 1,2-benzisoxazole-3-acetamide (49 g) and the mixture was refluxed for 1.5 hours. The excess phosphorus oxychloride was distilled off under a reduced pressure and the residue was added to icewater. The resulting precipitate was extracted with ether, and the ether layer was dried and distilled to remove ether to give the desired compound (41 g), which was recrystallized from benzene-hexane. m.p. 77° to 78°C.

D. 5-Methoxy-1,2-benzisoxazole-3-acetonitrile:

To phosphorus oxychloride (150 ml) was added 5-methoxy-1,2-benzisoxazole-3-acetamide (30 g) and the mixture was refluxed for 1.5 hours. The reaction mixture was added to ice-water and the resulting precipitate was extracted with benzene. The benzene layer was distilled under a reduced pressure to remove benzene to give the desired compound (26 g), which was recrystallized from benzene-hexane. m.p. 122° to 124°C.

E. Ethyl 1,2-benzisoxazole-3-acetimidate hydrochloride:

In ethanol (30 ml) was dissolved 1,2-benzisoxazole-3-acetonitrile (10 g) and the mixture was saturated with hydrogen chloride by passing through dry hydrogen chloride gas under ice-cooling. The mixture was allowed to stand at 5°C overnight. The precipitated ammonium chloride was filtered off and to the filtrate was added ether. The precipitated crystallines were separated by filtration, washed with ether and dried to give the desired compound (10.2 g). m.p. 107° to 109°C.

F. 1,2-Benzisoxazole-3-thioacetamide:

To a suspension of 1,2-benzisoxazole-3-acetamide (1.76 g) in toluene (20 ml) was added phosphorus pentasulfide (2.22 g), and the mixture was heated on oil bath at 110°C for 20 minutes. To the reaction mixture was added chloroform and the insoluble substance was filtered off. The filtrate was distilled under a reduced pressure to remove the solvent, and the oily residue was subjected to silica gel column chromatography and eluted with chloroform. The crystallines precipitated from the eluate was recrystallized from ethanol to give the desired compound (0.60 g). m.p. 139° to 142°C.

G. Methyl 1,2-benzisoxazole-3-thioacetimidate hydroiodide:

In acetone (30 ml) were dissolved 1,2-benzisoxazole-3-thioacetamide (0.58 g) and methyl iodide (4.2 g) and the mixture was refluxed on water bath at 90°C for 1 hour. After the reaction, the solvent was distilled off under a reduced pressure. The precipitated crystallines were separated by filtration, washed with ether and dried to give the desired compound (0.66 g). m.p. 158° to 165°C (decomp).

H. 1,2-Benzisoxazole-3-acetaldoxime:

In ethanol (200 ml) was dissolved metal sodium (4.2 g) and thereto was added hydroxylamine hydrochloride (11.8 g). To the solution was added a solution of 1,2-benzisoxazole-3-acetaldehyde (15 g) in ethanol (100 ml), and the mixture was heated at 75° to 80°C for 1 hour. After the reaction, the solvent was distilled off and to the residue was added ether and the insoluble substance was filtered off. The filtrate was concentrated and thereto was added n-hexane. The precipitated crystallines were recrystallized from ether-n-hexane to give the desired compound (10 g). m.p. 114° to 116°C.

I. 1,2-Benzisoxazole-3-acetohydroximic chloride:

To a solution of 1,2-benzisoxazole-3-acetaldoxime (0.5 g) in ether (20 ml) was passed through chlorine gas under ice-cooling for 20 minutes. The mixture was distilled under a reduced pressure to remove the solvent. The precipitated crystallines were separated by filtration, washed with ether and dried to give the desired compound (0.3 g).

J. 1,2-Benzisoxazole-3-acetohydroximic acid ethyl ester:

In absolute ethanol (50 ml) was dissolved metal sodium (0.85 g) and to the solution was added a solution of 1,2-benzisoxazole-3-acetohydroximic chloride (1.1 g) in ethanol (25 ml) under ice-cooling. After stirring for 1 hour under ice-cooling, the mixture was distilled under a reduced pressure to remove the solvent. To the residue was added water and the mixture was extracted with ether. The extract was washed with water, dried over anhydrous sodium sulfate and then distilled under a reduced pressure to remove the solvent to give the desired compound as an oily substance (0.5 g).

What is claimed is:

1. A 3-substituted-1,2-benzisoxazole of the following formula:

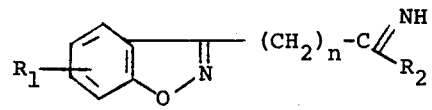

wherein $R_1$ is hydrogen, hydroxy, nitro, alkyl of 1 to 5 carbon atoms, alkoxy of 1 to 5 carbon atoms, halogen or amino; $R_2$ is hydroxyamino or an acyloxyamino selected from the group consisting of benzoyloxyamino, 3,4,5-trimethoxybenzoyloxyamino, ethoxycarbonyloxyamino and acetoxyamino; $n$ is an integer of 0 to 3; and the benzene ring may be substituted by 1 or 2, the same or different, group $R_1$, and its pharmaceutically acceptable acid addition salts.

2. An 0-acyl-3-substituted-1,2-benzisoxazole of the following formula:

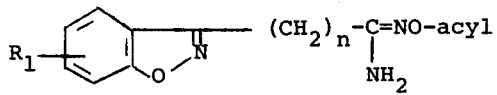

wherein $R_1$ is hydrogen, hydroxy, nitro, alkyl of 1 to 5 carbon atoms, alkoxy of 1 to 5 carbon atoms, halogen or amino; $n$ is an integer of 0 to 3; and acyl is a member selected from the group consisting of benzoyl, 3,4,5-trimethoxybenzoyl, ethoxycarbonyl and acetyl.

3. A 3-substituted-1,2-benzisoxazole of the following formula:

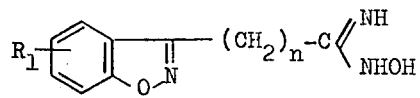

wherein $R_1$ is hydrogen, hydroxy, nitro, alkyl of 1 to 5 carbon atoms, alkoxy of 1 to 5 carbon atoms, halogen or amino; and $n$ is an integer of 0 to 3, and its pharmaceutically acceptable acid addition salts.

4. The 3-substituted-1,2-benzisoxazole according to claim 3, wherein $n$ is 1.

5. The 0-acylated-3-substituted-1,2-benzisoxazole according to claim 2, wherein $n$ is 1 and the acyl group is a member selected from the group consisting of benzoyl, ethoxycarbonyl and acetyl.

6. 1,2-Benzisoxazole-3-acetamidoxime and its pharmaceutically acceptable acid addition salts.

7. 0-Benzoyl-1,2-benzisoxazole-3-acetamidoxime and its pharmaceutically acceptable acid addition salts.

8. 6-Methoxy-1,2-benzisoxazole-3-acetamidoxime and its pharmaceutically acceptable acid addition salts.

9. 5-Fluoro-1,2-benzisoxazole-3-acetamidoxime and its pharmaceutically acceptable acid addition salts.

10. 1,2-Benzisoxazole-3-acetamidoxime.

* * * * *